United States Patent [19]

Bullivant

[11] Patent Number: 5,507,816
[45] Date of Patent: Apr. 16, 1996

[54] SPINAL VERTEBRAE IMPLANTS

[75] Inventor: Michael Bullivant, South Yorkshire, Great Britain

[73] Assignee: Customflex Limited, South Yorkshire, United Kingdom

[21] Appl. No.: 256,025

[22] PCT Filed: Dec. 1, 1992

[86] PCT No.: PCT/GB92/02232

§ 371 Date: Sep. 6, 1994

§ 102(e) Date: Sep. 6, 1994

[87] PCT Pub. No.: WO93/10725

PCT Pub. Date: Jun. 10, 1993

[30] Foreign Application Priority Data

Dec. 4, 1991 [GB] United Kingdom ............... 9125798

[51] Int. Cl.[6] ............................................. A61F 2/44
[52] U.S. Cl. ................................... 623/17; 606/61
[58] Field of Search ..................... 623/17, 16, 20; 606/61

[56] References Cited

U.S. PATENT DOCUMENTS 5,002,576  3/1991  Fuhrmann et al. .................. 623/17

FOREIGN PATENT DOCUMENTS 0176728  4/1986  European Pat. Off. ............. 623/17
3023353  4/1981  Germany ............................. 623/17

Primary Examiner—David Isabella
Attorney, Agent, or Firm—Sheridan Ross & McIntosh

[57] ABSTRACT

The present invention relates to a spinal implant having a plate with a raised platform which rests in a channel in a vertebrae to prevent sideways movement of the plate. A rib extends into a groove formed in the base of the channel to help prevent relative forwards and backwards movement of the plate through the channel. Another plate is similarly secured to the facing surface of an adjacent vertebrae. A spacer is inserted between the plates, such spacer including a downwardly facing convex surface and a flat upwardly facing surface. The convex surface slides in a concave recess provided on top of the plate and the flat surface slides against a downwardly facing flat surface of the upper plate.

8 Claims, 4 Drawing Sheets

SPINAL VERTEBRAE IMPLANTS

The present invention relates to a spinal implant, an implant and a spine incorporating an implant. The invention is particularly but not exclusively applicable to implants for spinal vertebrae such as human vertebrae.

A spinal vertebral disc replacement would be performed when one of the discs which lie between the bodies of the vertebrae, has become damaged or dislocated giving rise to what is commonly known as a "slipped disc". These cases tend to be treated by removing the old disc and packing the space with bone chips. The disadvantages of this method are the unreliability of the results and the loss of mobility experienced by the patient in the lower back.

The aim of a spinal disc prosthesis is to replace the damaged disc while maintaining function and stability in the patients back. There are at present very few spinal disc replacement systems available in the world. They comprise generally of a pair of metal plates, one of which is placed on the upper of the two vertebrae and the other on the lower. A polyethylene bearing is then pushed between the plates to provide stability with a degree of motion. The problems of existing systems are that the polyethylene component tends to be contoured (convex) on both sides which enables it to locate in two concave depressions, one each in the centre of the two plates. This requires that both plates be exactly in line with each other of the polyethylene insert cannot be located. In order that alignment can be consistently achieved, it is necessary to have complex instrumentation which makes the operation difficult to perform. The second major problem with existing systems is one of fixation of the metal plates to the bone of the vertebrae. Although once in place the components are under constant compression, this does not prevent rotation of the plates or sideways movement, both of which are extremely undesirable. To date this problem has been addressed by having small spikes on the back of the metal plates which are embedded in the bone. These however do not provide good fixation and could easily work loose, neither do they allow for any bony integration with the implant.

According to one aspect of the present invention a method of securing an implant into an animal bone comprises removing a portion of the bone of form a first pair of spaced opposed generally planar abutment surfaces which face each other and locating the implant such that the implant engages with the abutment surfaces to restrict movement of the implant relative to the bone in a direction towards either abutment surface.

The abutment surfaces may be substantially parallel to each other.

The method may comprise removing substantially all of the bone between the abutment surfaces and locating the implant to substantially fill the space between the abutment surfaces.

The method may comprise removing a portion of the bone to form a second pair of spaced opposed abutment surfaces which extend at an angle to the first pair of abutment surfaces and locating the implant such that the implant engages with the second pair of abutment surfaces to restrict movement of the implant in the direction towards either of the second pair of abutment surfaces.

A second pair of spaced opposed abutment surfaces may face each other. The second pair of abutment surfaces may be formed by a rotating drill.

The second pair of abutment surfaces may be located in a part of the bone which is exposed only after the formation of the first pair of abutment surfaces.

The method may comprise forming a first pair or a first and second pair of abutment surfaces as previously referred to in a second bone with a different component of the implant being arranged to engage with the first or the first and second abutment surfaces.

The method may comprise securing the implant to a vertebrae such as a human vertebrae.

The present invention also includes a combination comprising a bone and an implant in which the implant has been secured by a method as herein referred to.

According to another aspect of the present invention an implant comprises a first pair of spaced opposed generally planar abutment surfaces which face away from each other, the abutment surfaces being arranged to abut with correspondingly spaced opposed generally planar abutment surfaces of a bone which face each other.

The planar abutment surfaces may be substantially parallel to each other.

The implant may include a second pair of spaced abutment surfaces which extend at an angle to the first pair and which are also arranged to abut with correspondingly spaced opposed generally planar abutment surfaces of a bone. The second pair of surfaces may be comprised by an elongate rib of partially arcuate cross-section.

The first, or alternatively, the first and second pairs of abutment surfaces may be comprised on a first component.

The implement may include a third pair of spaced abutment surfaces spaced from the first and second pairs the third pair of abutment surfaces facing away from each other, the third pair of abutment surfaces being arranged to abut with correspondingly spaced opposed generally planar abutment surfaces of a bone which face each other. The planar abutment surfaces with which the third pair are arranged to cooperate may be substantially parallel to each other. The implant may include a fourth pair of spaced abutment surfaces which extend at an angle to a third pair and which are also arranged to abut with correspondingly spaced opposed generally planar abutment surfaces of a bone. The fourth pair of abutment surfaces may be comprised by an elongate rib of particularly arcuate cross-section. The third or, alternatively, the third and fourth pairs of abutment surfaces may be comprised on a second component of the implant.

The implant may be arranged to cooperate with surfaces of a spinal bone.

According to a further aspect of the present invention a spinal implant comprises a first component arranged, in use, to be secured to a first vertebrae and a second component arranged, in use, to be secured to a second vertebrae, the first and second components being arranged, in use, to move both transversely and in a curved direction relative to each other.

The relative transverse and curved movements may be arranged to occur simultaneously.

The components may be arranged to move transversely relative to each other in two different directions. The components may be arranged to move in a curved direction relative to each other in an least two different directions.

The implant may include an intermediate component arranged to be located between the first and second component, the intermediate component being arranged, in use, to move in a transverse direction relative to the first component and in a curved direction relative to the second component. The intermediate component may include a generally planar surface arranged to slide against a generally planar surface of the first component. The intermediate component may include a curved surface arranged to slide in a correspondingly inversely shaped curved surface of the second component. The curved surface may be part spherical. The curved surface of the intermediate component may be convex and that of the second component may be concave.

According to another aspect of the present invention a spine incorporates a spinal implant located between adjacent vertebrae comprises adjacent vertebrae moving transversely and in a curved direction relative to each other.

The spine may comprise the transverse and curved relative movement occurring simultaneously.

According to another aspect of the present invention a method of attaching a spinal implant to two adjacent vertebrae comprises securing a first and second component of the implant to respective adjacent vertebrae and locating an intermediate component between the first and second components.

The method may comprise the intermediate component being selected from one of a plurality of intermediate components of different sizes.

The present invention includes any combination of the herein referred to features or limitations.

The present invention may be carried into practice in various ways, but one embodiment will now be described by way of example and with reference to the accompanying drawings in which:

FIGS. 1a and 1b are a front and a side view respectively of an implant assembly comprising an upper plate 10, a lower part or plate 14 and a spacer 12, the assembly being located between spaced vertebrae 16 and 18;

Figure 1A:
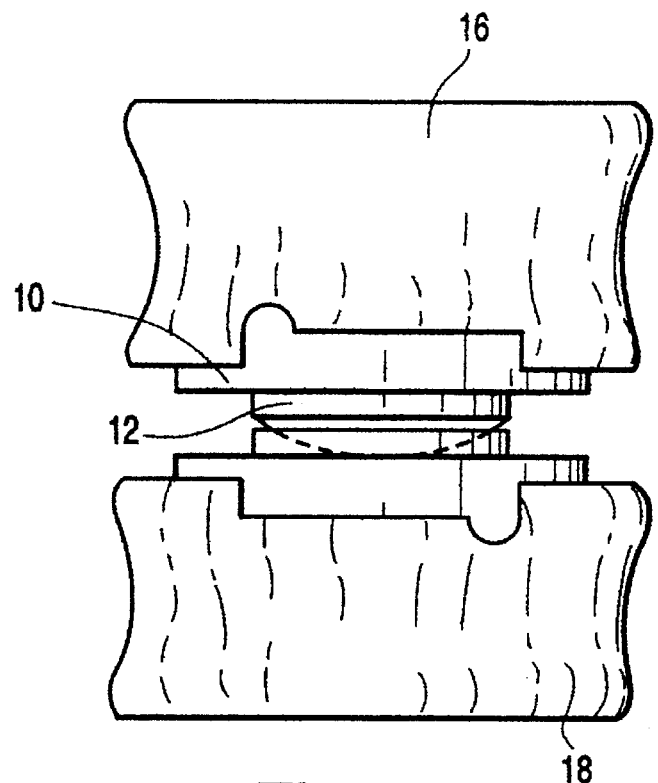
Figure 1B:
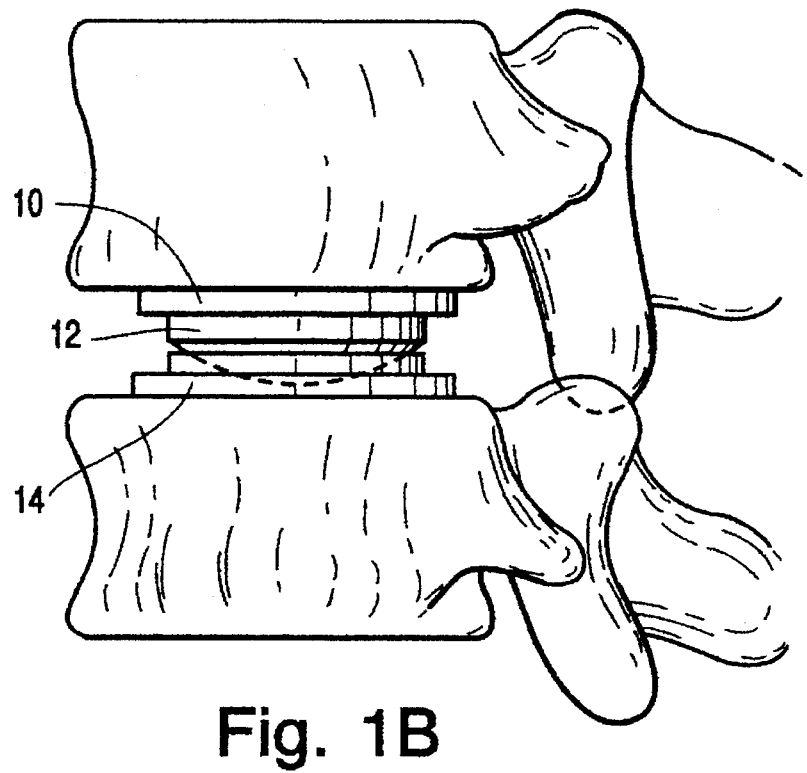
Figure 2A:
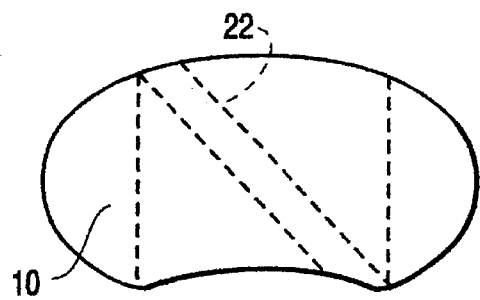
FIGS. 2a, 2b, 2c, 2d and 2e are an /underneath, front, side, front and plan view respectively of the upper plate 10.
Figure 2B:
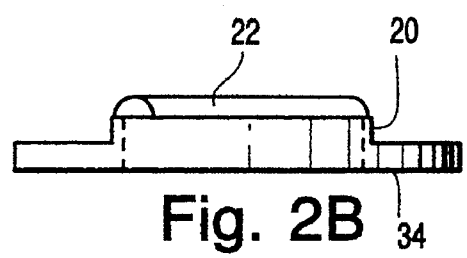
Figure 2C:
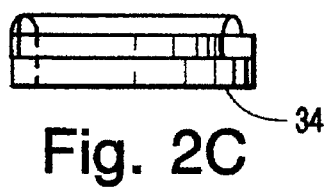
Figure 2D:
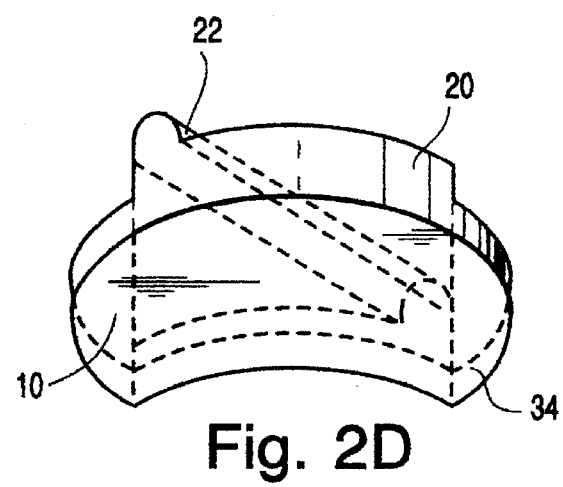
Figure 2E:
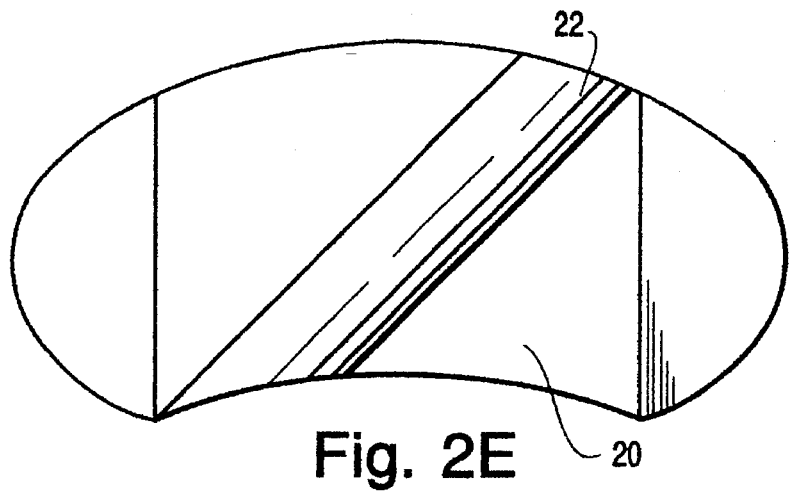

As shown in FIG. 1, the implant assembly comprises the upper and lower plates 10 and 14 and the spacer 12. The way in which the components of the assembly co-operate will be described later, and the fixing of the plates 10 and 14 to their respective vertebrae will now be described.

The vertebrae are first accessed through the abdominal region of the patient and the two vertebrae 16 and 18 are clamped in a common jig (not shown) which restrains the vertebrae against relatively translational or rotational movement.

The jig is provided with aligned guides in order that a rectangular channel can be removed from the facing surfaces of each vertebrae. The bone is removed with conventional techniques such as "shaving" with a chisel. The channels extend from the front to the rear of the vertebrae and the side walls of the channels prevent the plates from sliding in a direction transverse to the extent of the channels. The channel is removed in order to take away the periosteum (the outer bone membrane) and the cortex (the hard outer shell) and to expose the cancellous (the honeycomb of blood and fat).

An angled semicircular groove is then cut in the facing surfaces of each rectangular channel. The semicircular grooves are cut by pushing a rotating drill through guide holes in the jig which control precisely the location of the grooves.

The vertebrae are now ready for the attachment of the plates.

As shown in FIGS. 2a to 2e the upper plate 10 is provided with a raised platform 20 having a width and depth corresponding to those dimensions of the channel in the bone to restrict sideways movement of the plate. The plate 10 also includes a semicircular rib 22 extending upwardly from the top of the platform at an angle to the sides of the platform. The rib 22 corresponds in direction and dimension to the groove which has been cut in the vertebrae 16 and helps prevent relative movement *forwards and backwards in the direction of the channel.

Accordingly, when the plate 10 is offered to the vertebrae 16, the sides of the channel guide the plate in the front to back direction and the plate can only be pushed up into full engagement with the vertebrae 16 when the rib 22 is aligned with the semicircular groove in the vertebrae in order that the rib can fill the groove.

The lower plate 14 is attached to the vertebrae 18 in much the same way. Thus a channel and semicircular groove are cut in the upwardly facing surface of the vertebrae, and the plate 14 is provided with a downwardly facing platform 24 and a semicircular rib 26 which co-operate with the channel and groove cut in the bone in order to locate the plate 14 on the bone.

The platforms and ribs of the parts 10 and 14 can be sprayed with titanium to provide a rough, hard finish. Before the plates are fixed to the bone surfaces of the plate which are to co-operate with the bone they may be coated with Hydroxy Apatite, a calcium based material, which helps to prevent rejection by the body of the implant and which assists in the bonding of the parts to the bone.

The parts 10 and 14 are now secured to the vertebrae in a precisely spaced and aligned relationship with lateral or rotational movement of each part relating to its supporting bone being prevented by abutment of co-operating parts.

Figure 3A:
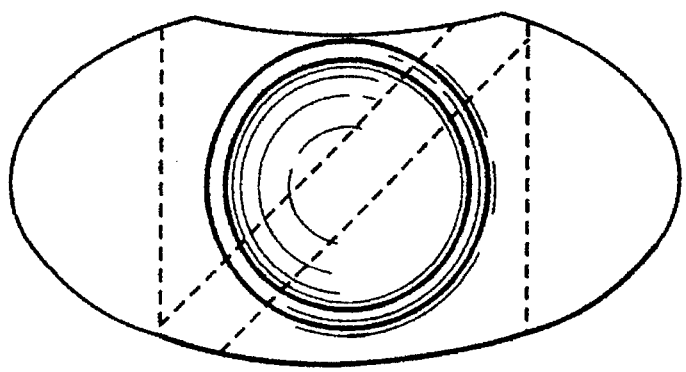
FIGS. 3a, 3b, 3c and 3d are a plan, front, side and front perspective view respectively of the lower plate 14.
Figure 3B:
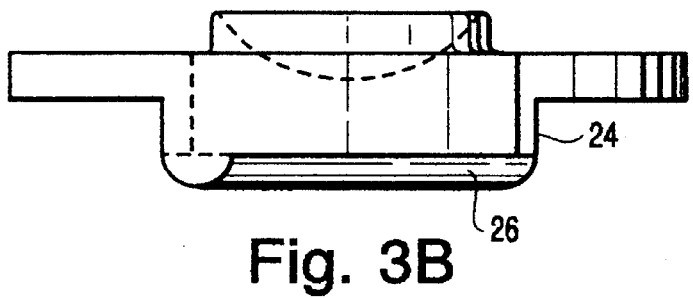
Figure 3C:
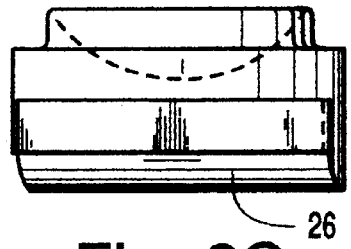
Figure 3D:
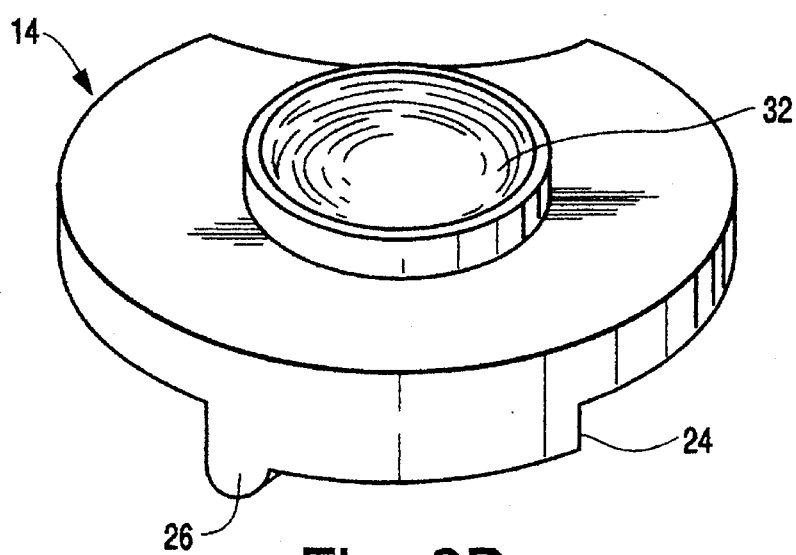
Figure 4A:
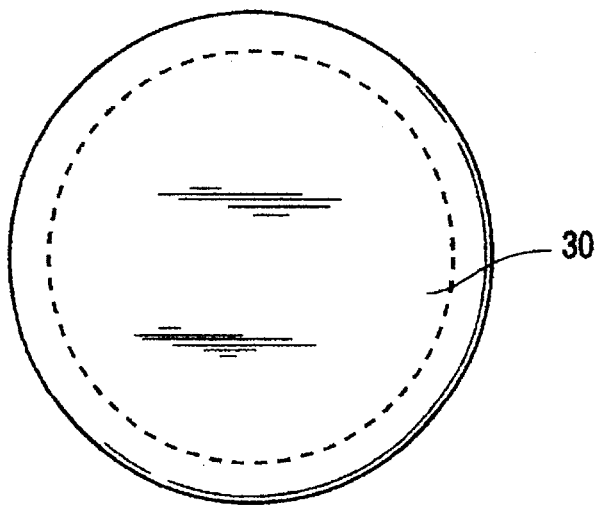
FIGS. 4a, 4b, 4c and 4d are a plan, front, side and front perspective view respectively of the spacer 12.
Figure 4B:
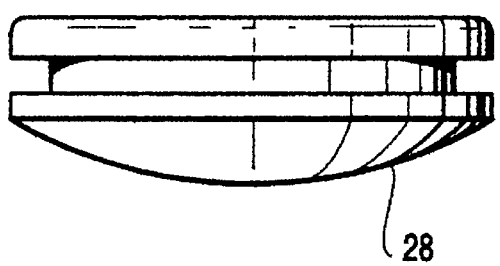
Figure 4C:
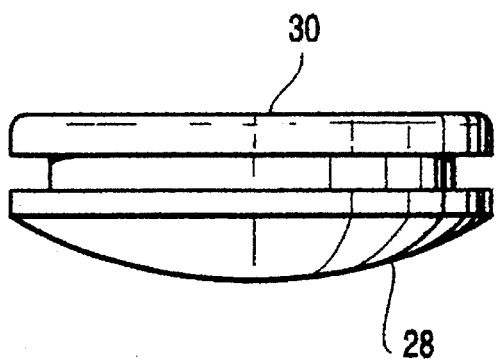
Figure 4D:
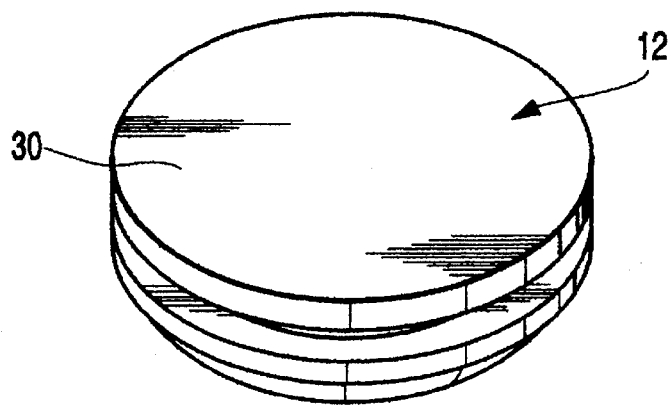

The spacer 12 of polyethylene is then inserted between the parts 10 and 14. As shown in FIGS. 1a and 1b and FIGS. 4a to d, the spacer includes a downwardly facing convex surface 28 and a flat upwardly facing surface 30. The convex surface 28 is arranged to slide in a concave recess 32 (see FIG. 3d) provided on the top of the part 14. The flat surface 30 is arranged to slide against a downwardly facing flat surface 34 of the upper part 10. The thickness of the spacer 12 can be varied to suit the particular requirement of the patient. The natural tension in the vertebrae ensures that the vertebrae are biased together to trap the spacer in place.

The co-operating convex and concave surfaces of the spacer 12 with the plate 14 allows the vertebrae 18 to pivot relative to each other. The co-operating flat surfaces of the spacer 12 and the plate 10 allows the vertebrae to slide transversely in the plane of those co-operating surfaces. This transverse sliding movement is the first such movement that the applicant is aware of which is provided in implants. Traditional medical opinion is that no such movement should be allowed as none would appear to occur in a healthy spinal system. However, the mechanics of spinal operations are extremely complicated and the operation to gain access to the vertebrae can alter the governing parameters as the spine muscles are cut. Accordingly that muscle tissue will scar and the muscles no longer act on the vertebrae in the conventional way. It is believed that the provision of a small amount of transverse sliding movement between the vertebrae enables considerable transverse forces which can act between vertebrae having conventional implants to be relieved thereby reducing stress on the attachment of the plates to the vertebrae.

Although the upper and lower plates are extremely accurately aligned relative to each other, an additional advantage of providing relative transverse movement is that, as the spacer can slide relative to the plate 10 the components can move to find their own alignment position, should that not be exactly where the previous aligned position was, for example.

It can be seen that the concave and convex surfaces extend through approximately 90° and thus there is virtually no chance of the implant escaping from between the plates under normal pivotal movement of the vertebrae.

I claim:

1. A spinal implant comprising a first component arranged, in use, to be secured to a first vertebrae and a second component arranged, in use, to be secured to a second vertebrae said implant including a first pair of cooperating surfaces that are curved in at least two directions and a second pair of cooperating surfaces that are substantially planar, whereby, in use, relative movement of said first pair of cooperating surfaces is arranged to allow curved movement of said first and second components to occur in more than one possible direction and relative movement of said second pair of cooperating surfaces is arranged to cause relative translational movement of said first and second components.

2. An implant as claimed in claim 1 in which the relative transverse and curved movements are arranged to occur simultaneously.

3. An implant as claimed in claim 1 in which the components are arranged to move transversely relative to each other in two different directions.

4. An implant as claimed in claim 1 including an intermediate component arranged to be located between the first and second components, the intermediate component being arranged, in use, to move in a translational direction relative to the first component and in a curved direction relative to the second component.

5. An implant as claimed in claim 4 in which the intermediate component includes a generally planar surface arranged to slide against a generally planar surface of the first component.

6. An implant as claimed in claim 4 in which the intermediate component includes one of said cooperating surfaces of said first pair arranged to slide in said other of said cooperating surfaces of said first pair, which said other surface comprises a correspondingly inversely shaped curved surface of said second component.

7. An implant as claimed in claim 6 in which said first pair of cooperating surfaces have a spherical shape.

8. An implant as claimed in claim 6 in which the curved surface of the intermediate component is convex and that of the second component is concave.

* * * * *